United States Patent [19]

Winston et al.

[11] Patent Number: 5,411,551
[45] Date of Patent: * May 2, 1995

[54] STENT ASSEMBLY WITH SENSOR

[75] Inventors: Thomas R. Winston, Leadwood; John M. Neet, Shawnee, both of Kans.

[73] Assignee: Ultrasonic Sensing and Monitoring Systems, Inc., Kansas City, Mo.

[*] Notice: The portion of the term of this patent subsequent to Apr. 26, 2011 has been disclaimed.

[21] Appl. No.: 127,806

[22] Filed: Sep. 28, 1993

Related U.S. Application Data

[63] Continuation-in-part of Ser. No. 925,959, Aug. 5, 1992, Pat. No. 5,306,294.

[51] Int. Cl.6 .................................................. A61F 2/06
[52] U.S. Cl. ............................................ 623/1; 623/12;
128/635; 606/191; 606/194
[58] Field of Search .................... 623/1, 12; 128/635,
128/662.06; 606/108, 191, 192, 194

[56] References Cited

U.S. PATENT DOCUMENTS

| 4,696,458 | 9/1987 | Wiktor . | |
|---|---|---|---|
| 4,733,665 | 3/1988 | Palmaz . | |
| 5,007,926 | 4/1991 | Derbyshire . | |
| 5,019,085 | 5/1991 | Hillstead . | |
| 5,026,377 | 6/1991 | Burton et al. . | |
| 5,041,126 | 8/1991 | Gianturco . | |
| 5,078,720 | 1/1992 | Burton et al. . | |
| 5,100,429 | 3/1992 | Sinofsky et al. . | |
| 5,108,417 | 4/1992 | Sawyer . | |
| 5,117,831 | 6/1992 | Jang et al. | 128/662.06 |
| 5,147,370 | 9/1992 | McNamara et al. . | |
| 5,151,105 | 9/1992 | Kwan-Gett | 623/1 |
| 5,159,920 | 11/1992 | Condon et al. | 128/662.06 |
| 5,190,041 | 3/1993 | Palti | 128/635 |
| 5,211,658 | 5/1993 | Clouse | 606/191 |
| 5,265,601 | 11/1993 | Mehra | 607/9 |
| 5,306,294 | 4/1994 | Winston et al. | 623/1 |

FOREIGN PATENT DOCUMENTS 9115254 10/1991 WIPO .
9117789 11/1991 WIPO .

Primary Examiner—Paul Prebilic
Attorney, Agent, or Firm—Hovey, Williams, Timmons & Collins

[57] ABSTRACT

A stent/sensing device is provided by attachment of an in vivo sensor such as a blood glucose sensor to the inner surface of the multiple layer roll. Electrical leads extending from the sensor device pass through an elongated groove provided in the inner supporting spool for the stent.

8 Claims, 2 Drawing Sheets

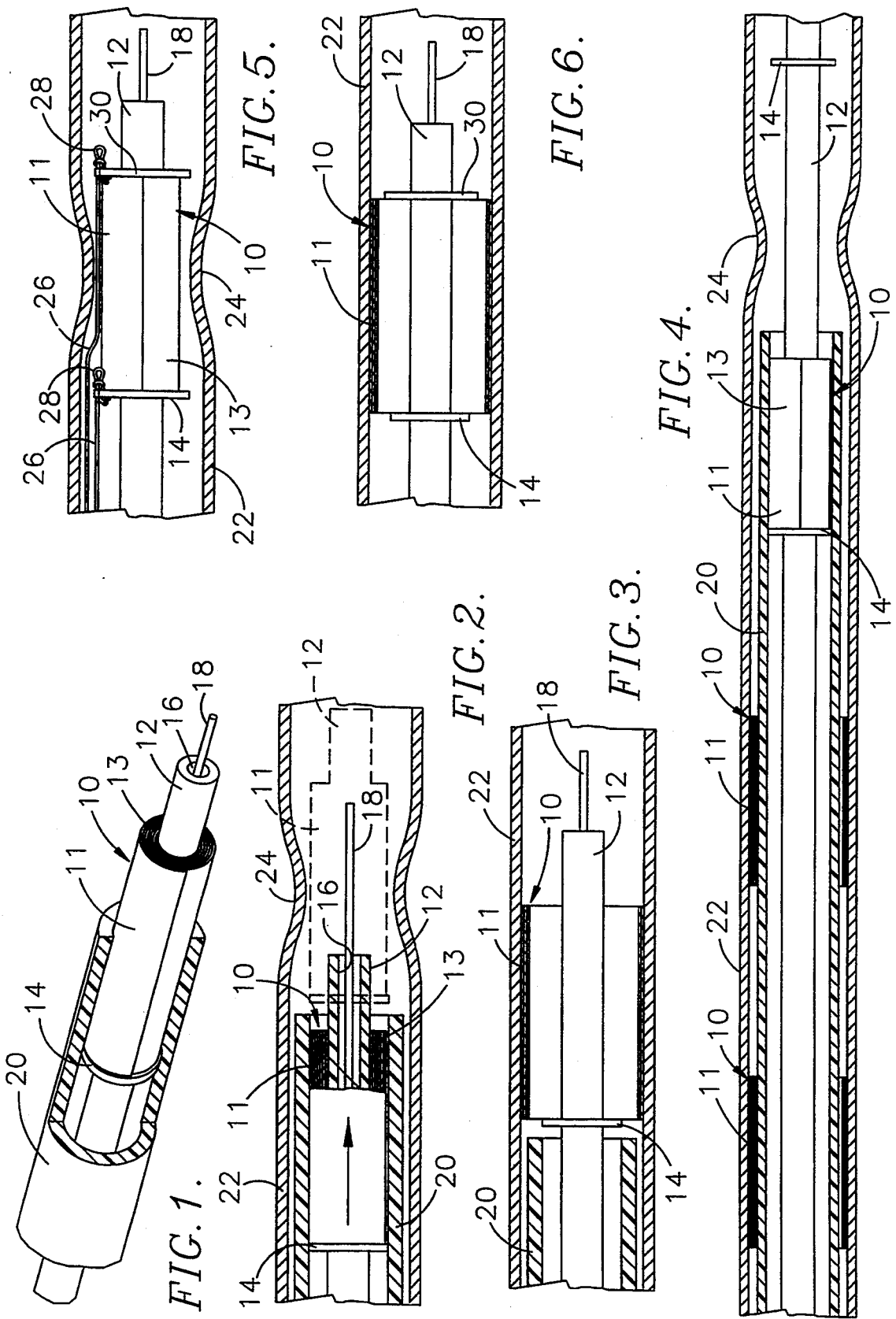

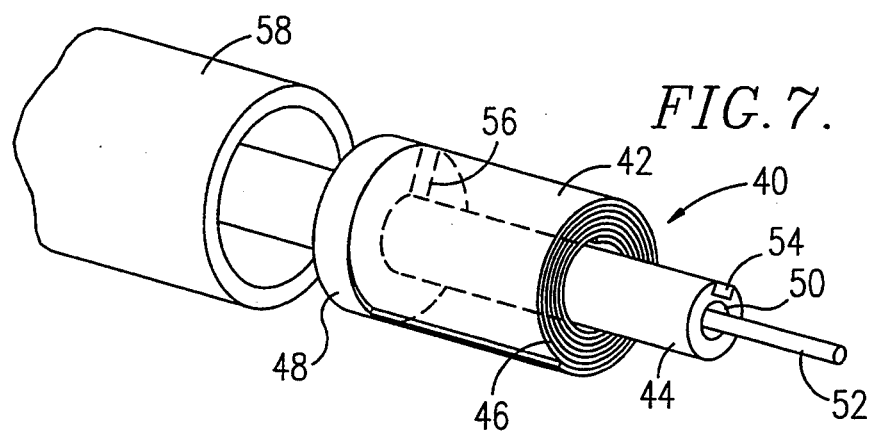
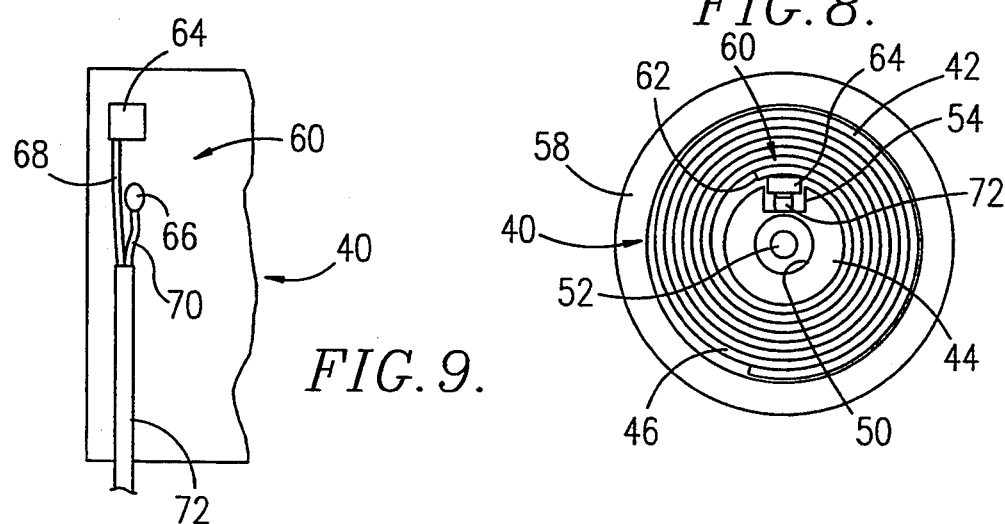
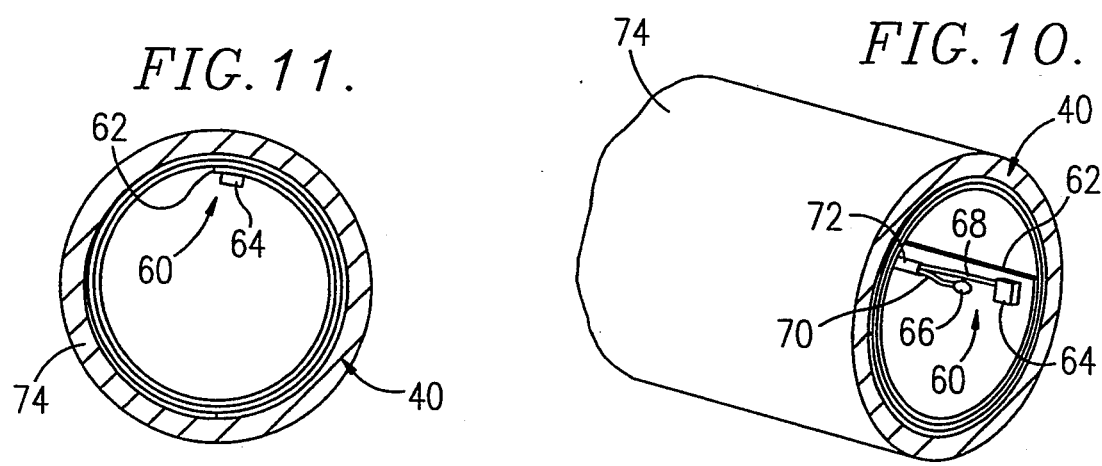

STENT ASSEMBLY WITH SENSOR

RELATED APPLICATION

This is a continuation-in-part of application Ser. No. 07/925,959 filed Aug. 5, 1992, now U.S. Pat. No. 5,306,294, and entitled "Stent Construction of Rolled Configuration."

BACKGROUND OF THE INVENTION

1. Field of the Invention

This invention relates in general to the field of medical implants and more particularly to a stent which is constructed in an improved manner for simple and effective placement in a body passage to reinforce a damaged area.

In another aspect of the invention, stent assemblies are provided which include sensing devices such as blood glucose sensors.

2. Description of the Prior Art

Tubular prostheses commonly known as stents have been used to reinforce and strengthen damaged blood vessels and other body passages. For example, the blood vessels can collapse, dilate, become partially occluded or otherwise damaged by disease or other causes. The presence of an aneurysm or stricture in the blood vessel often requires implantation of a stent to strengthen the vascular wall in the area of the damage. Other passages in the body can also sometimes benefit from stent implantation, including the esophagus, the trachea, the gastro intestinal tract, the bile duct, the ureter and the urethra.

The benefits of self-expanding stents have been recognized. A self-expanding stent is held in a contracted state until it has been positioned properly, typically with the aid of an instrument such as a catheter. After the stent has been placed properly in the damaged blood vessel, it is allowed to expand against the damaged vessel wall in order to reinforce the damaged area. Examples of self-expanding stents are disclosed in U.S. Pat. Nos. 5,026,377 and 5,078,720 to Burton et al., U.S. Pat. No. 5,019,085 to Hillstead, U.S. Pat. No. 4,969,458 to Wiktor, and U.S. Pat. No. 5,041,126 to Gianturco. The Wicktor and Gianturco stents are in the form of coiled or looped wires that are unable to contact the entirety of the weakened vessel wall. The same is true of the Hillstead stent which takes the form of a multiple loop wire structure. The stents disclosed in the two Burton patents are braided structures that are likewise incapable of contacting the entirety of the damaged vessel wall. All of the stents and particularly their placement means are complicated to construct, and the stents are difficult to place precisely in the damaged vessel.

A number of attempts have been made in the past to develop in vivo sensors for continuously monitoring various conditions. To give but one example, a large number of glucose sensors have been proposed in the past for use by diabetic patients. Such sensors are designed to continuously monitor glucose levels in the blood. Prior devices of this character have been plagued by a number of deficiencies, most notably inaccuracies and the inability for invasive sensors to remain in place over long periods of time.

SUMMARY OF THE INVENTION

The present invention is directed to an improved stent which is particularly characterized by a stronger construction, the ability to provide a solid and continuous wall that lines the entirety of the damaged part of passage wall in which it is implanted, and by ease and accuracy of placement. In accordance with the invention, a stent is provided in the form of a flexible metal sheet which is closely wound around a spool in a spinal roll. A sheath initially surrounds the roll in order to retain it in a contracted states. The spool, stent and sheath can be inserted together into the body with the spool following a guide wire until it is located adjacent to the damaged area. Then, the sheath is held stationary while the spool is pushed out the end of the sheath, with a flange on the spool making certain that the tightly coiled roll remains on the spool. Once the spool has cleared the sheath, the roll is released and allowed to expand against the damaged wall of the vessel. The sheath and spool can then be withdrawn, leaving the stent in place.

An alternative embodiment of the invention eliminates the sheath and instead holds the stent in its retracted states by means of a pair of control cords which are connected by slip knots to flanges on the spool located adjacent to the opposite ends of the stent. When the stent has been properly positioned, the cords can be pulled to release the slip knots and allow the stent to expand against the vessel wall. In both embodiments, multiple stents can be carried on the same spool if it is necessary to strengthen the vessel in more than one area.

Because the stent takes the form of a continuous sheet, the stent essentially contacts the entirety of the damaged vessel wall area, rather than simply reinforcing the damaged area as is the case with looped or coiled wires or braided netting type structures. In addition, the stent preferably has multiple layers that bear against one another when the stent is in its expanded condition. This further enhances the strength of the stent and provides multiple layers that are held against one another by friction resulting from the tendency for the stent to expand under the influence of internal spring force.

The method by which the stent is placed in the proper position and allowed to expand against the vessel wall is improved in a number of respects compared to what has been proposed in the past. The placement method is simple and accurate and does not involve complexities such as the need to inflate a balloon catheter or other mechanism.

In another aspect of the invention a stent including a sensing device is provided. To this end, the sensing unit is advantageously affixed proximal to the inner margin of the rolled stent sheet, and the stent core is provided with a recess for accommodating electrical leads. In practice, the stent is placed within a vascular vessel in the manner described above, and upon stent expansion the inboard sensor is properly placed for accurate, long term monitoring of the desired condition. The invention finds particular utility in connection with glucose sensing devices.

BRIEF DESCRIPTION OF THE DRAWINGS

In the accompanying drawings which form a part of the specification and are to be read in conjunction therewith and in which like reference numerals are used to indicate like parts in the various views;

FIG. 1 is a fragmentary perspective view of a stent and placement system for the stent, all constructed according to a preferred embodiment of the present invention, with the stent in its retracted condition and part of the sheath shown in section for purposes of illustration;

FIG. 2 is a fragmentary sectional view illustrating the stent being applied to a stricture in a blood vessel, with the broken lines depicting the spool and stent pushed out the end of the sheath;

FIG. 3 is a fragmentary sectional view similar to FIG. 2, but showing the stent expanded against the damaged vessel well prior to withdrawal of the sheath and spool;

FIG. 4 is a fragmentary sectional view showing an alternative embodiment of the invention in which the spool is constructed to carry multiple stents and to apply them to multiple damaged areas of a blood vessel;

FIG. 5 is a fragmentary sectional view of a stent arrangement constructed according to an alternative embodiment of the invention, with the stent in its retracted condition and positioned properly for application to a damaged stricture in a blood vessel;

FIG. 6 is a fragmentary sectional view similar to FIG. 5, but showing the stent released and expanded against the damaged vessel wall prior to withdrawal of the spool;

FIG. 7 is an enlarged, fragmentary isometric view illustrating the stent and sensor assembly of the invention, illustrated in its contracted condition disposed about an innermost spool, as the assembly is ejected from a surrounding sheath;

FIG. 8. is an end view of the assembly depicted in FIG. 7, but illustrating the contracted stent within the confines of the surrounding sheath;

FIG. 9 is a fragmentary enlarged view illustrating the attachment of a sensing device adjacent the inner margin of the rolled stent-defining sheet;

FIG. 10 is a an enlarged, fragmentary, isometric view illustrating the stent assembly of the invention in its expanded condition within a vascular vessel; and FIG. 11 is an end view of the expanded stent assembly illustrated in FIG. 10.

DETAILED DESCRIPTION OF THE INVENTION

Referring now to the drawings in more detail and initially to FIG. 1 in particular, numeral 10 generally designates a stent which is constructed in accordance with a preferred embodiment of the present invention. The stent 10 takes the form of an initially flat metal sheet which is wound tightly around a core which is in the form of a tubular spool 12. The stent 10 is preferably constructed of a stainless steel foil which is commercially available under the trade designation PH15-7, Condition CH900. The thickness of the sheet 11 is preferably about 0.0005 inch. When the sheet 11 is coiled around the spool 12, it is in the shape of a spiral roll 13, and its outside diameter may be approximately 1.5 millimeter. The sheet 11 is long enough that there are approximately six or seven layers of the sheet which overlap one another when the roll 13 is in the contracted position shown i FIGS. 1 and 2. The roll presents a plurality of adjacent arcuate layers of the sheet in a direction transverse to the longitudinal axis of the core.

The sheet 11 produces an inherent spring force which tends to expand the sheet from the retracted condition of the roll 13. By way of example, it is contemplated that the sheet will initially be rolled to a diameter of approximately 5 millimeters and then heat treated in that condition in order to relax the internal stresses that are induced by winding the sheet to a partially contracted condition. Following the heat treatment, the material can be rolled into the tighter roll 13 (approximately 1.5 millimeter in diameter), and the roll will have fewer internal stresses than if it were initially wound into the tight 1.5 millimeter cylinder. The internal spring force of the roll 13 will tend to cause it to unwind to an expanded condition in which its diameter is approximately 5 millimeters (the diameter at which the heat treatment takes place).

The sheet 11 is wound tightly on the spool 12 near one end of the spool, and one end of the roll 13 butts against a flange 14 which is formed on the spool 12 at a location spaced from the end of the spool. The flange 14 projects radially from the spool 12 and has a diameter approximately equal to the diameter of the stent 10 in its fully contracted condition. The flange 14 is spaced from the end of the spool a distance greater than the axial length of the stent 10. The spool 12 is provided with a central axial passage 16 which receives a guide wire 18. As will be explained more fully, the spool 12 can be moved along the guide wire 18 in order to properly position the stent 10.

The stent 10 is maintained in its fully contracted position by an elongated sheath 20 having a tubular shape. The sheath 20 has an inside diameter substantially equal to the outside diameter of the stent 10 ion its fully retracted condition. The spool 12 and stent 10 are located within the sheath 20, with the outer surface of the stent 10 in contact with the inside surface of the sheath 20. The sheath 20 has a tubular form in order to receive the stent 10 and spool 12. The outside diameter of the sheath 20 is preferably somewhat smaller than the body passage in which the stent 10 is to be implanted. The spool 12 and sheath 20 are long enough that they can be advanced into a vessel to the area which is to be treated with the stent while the ends remain outside of the body.

In use, the sheath 20, with the stent 10 and spool 12 inside of it, is inserted into the body and advanced until its end is adjacent to an area of body passage in which the stent is to be implanted. For example, with reference to FIG. 2, the sheath 20 may be inserted through a blood vessel 22 until the leading end of the sheath is adjacent to the damaged area such as the stricture 24. The advance of the sheath 20 is then stopped, and the tube 12 is advanced while the sheath 20 remains stationary. As the tube is thus pushed out through the end of the sheath 20, the spool carries the stent 10 with it because the flange 14 pushes the stent forwardly along with the spool. Once the flange 14 and the entirety of the stent 10 have cleared the end of the sheath 20 in the position shown in broken lines in FIG. 2, there is no longer anything restraining the stent 10 against expansion. At this time, the stent is aligned with the stricture 24.

Because the stent is no longer held against expansion, it expands naturally under the influence of its inherent spring force to the full diameter of the vessel 22. In the fully expanded condition of the stent shown in FIG. 3, its outside surface contacts the inside surface of the vessel wall and effects expansion of the stricture 24.

It is noteworthy that the sheet construction of the stent 10 allows it to line the entirety of the damaged surface of the vessel 22 at the stricture 24 and the adjacent areas of the vessel wall. In this manner, the stent is able to remove the occlusion in the vessel that is caused by the stricture 24 and is also able to reinforce and strengthen the damaged vessel area at and near the stricture 24. Normal circulation through the vessel is thus restored. Rather than holding the sheath 20 stationary and pushing the stent out through its end, the sheath can be advanced until the stent is aligned with the damaged area, and the sheath can then be retracted while the spool 12 and stent 10 are held stationary. When the sheath is withdrawn far enough to release the stent, the stent expands in the manner previously indicated.

In the fully expanded condition of the stent, there are preferably at least two overlapping layers which bear against one another over a substantial proportion of their circumference of an inner layer and are held against one another by friction caused by the tendency of the stent to expand to its undeformed condition. These overlapping layers assure that the stent will be securely held in place and provide enhanced structural integrity by reason of the multiple layer structure that is implanted in the damaged area of the vessel. Once the stent has fully expanded, the sheath 20 and the tube 12 can be removed from the vessel, along with the guide wire 18. In its fully expanded condition, the diameter of the stent is at least as great as the inside diameter of the vessel so that when the stent expands into contact with the damaged vessel wall, it is held securely against the roll under the influence of its inherent spring force.

FIG. 4 depicts an arrangement which is for the most part identical to that shown in FIGS. 1–3. The principal difference is that the FIG. 4 construction has a spool 12 which is provided with a number of spaced apart stents 10 carried adjacent to different flanges 14. In use of the embodiment shown in FIG. 4, the stents 10 are applied in series to different weakened or damaged areas of the vessel 22, thereby strengthening the different damaged areas of the vessel to which the stents are applied. Virtually any desired number of stents can be carried on the spool 12.

FIGS. 5 and 6 depict an alternative embodiment of the invention in which the sheath 20 is not present. In place of the sheath, the function of holding the roll 13 in its contracted condition is performed by a pair of control cords 26. One of the control cords 26 is fitted through the flange 14 and is provided with a slip knot 28 which is formed adjacent to the flange and which bears against the outer layer of the stent 10 in a manner to prevent the stent from expanding. The other control cord 26 is extended through a second flange 30 which is spaced from flange 14 a distance slightly greater than the length of the stent 10. The ends of the cords 26 opposite the slip knots 28 remain outside the vessel.

In use of the embodiment shown in FIGS. 5 and 6, the spool 12 is extended into the vessel until the stent 10 is aligned with the stricture 24. Then, the control cords 26 are pulled to release the slip knots 28, thereby releasing the stent 10 which then expands naturally under the influence of the internal spring force to which it is subjected. The stent expands to the fully expanded condition shown in FIG. 6 in which it expands the stricture 24 and eliminates the occlusion presented by the stricture. In addition, the stent 10 lines the vessel and strengthens and reinforces the damaged vessel wall in the area of the stricture in the same manner indicated previously. Once the stent has been fully expanded, the spool 12 and guide wire 18 can be withdrawn from the vessel.

Attention is next directed to FIGS. 7–10, which illustrate another embodiment in accordance with the invention, namely a combination rolled stent and sensor 40. The assembly 40 includes an initially flat, thin metallic sheet 42 which is spirally and tightly wound around a core in the form of an elongated tubular spool 44. The sheet 42 is preferably stainless steel foil of the type described with reference to stent 10 of the earlier embodiment. As illustrated in FIG. 7, when the sheet 42 is coiled around spool 44, it is in the shape of a spiral roll 46 having an outside diameter of, e.g., 1.5 mm. The sheet 42 is of sufficient length to present approximately six or seven layers or sheet which overlap one another when the roll 46 is in the contracted position illustrated in FIGS. 7–8.

The sheet 42 produces an inherent spring force which tends to expand the sheet from the retracted condition of the roll 46, just as in the case of stent 10. The preferred means of manufacture, and the expansion dimensions, of the preferred stent 40 are likewise as described with reference to stent 10.

As best seen in FIG. 7, the sheet 42 is wound tightly on spool 44 adjacent one end thereof, and one end of the roll 46 abuts a flange 48 located in spaced relationship to the outboard end of the spool. The flange 48 projects radially from spool 44 and has a diameter approximately equal to the diameter of the stent 40 in its fully contracted condition. Also, flange 48 is spaced from the end of the spool 44 a distance greater than the axial length of the stent 40. The spool 44 is provided with a central axial passage 50 which receives a guide wire 52. In addition, the spool 44 has an elongated, axially extending, outer groove 54 along the length thereof. This groove communicates with a similar groove 56 provided through the flange 48.

The stent 40 is maintained in its fully contracted condition by means of an elongated, tubular sheath 58 having an inside diameter substantially equal to the outside diameter of the stent in its contracted condition. The spool 44 and stent 40 are located within the sheath 58, with the outer surface of the stent 40 in contact with the inside surface of the sheath 58. The outside diameter of the sheath 58 is preferably somewhat smaller than the body or vascular passage in which the stent 40 is to be implanted. The spool 44 and sheath 58 are long enough to permit advancement into the appropriate body or vascular vessel, while the ends thereof remain outside of the body.

A sensing device broadly referred to by the numeral 60 is affixed (e.g., by conventional adhesive) to the inner surface of sheet 42 adjacent the inner margin 62 thereof. As explained previously, the sensor 60 may be any one of a number of desired devices, e.g., a glucose sensor as shown. This latter sensor includes a pair of terminals 64, 66, with the terminal 64 housing otherwise conventional circuitry for the measurement of blood glucose. A pair of electrical leads 68, 70 extend from the terminals 64, 66 and are housed within a common flexible sheath 72. As best illustrated in FIG. 8, the sensing device 60, as well as the sheathed leads 68, 70 pass along the length of stent 40 and are accommodated by groove 54 provided in spool 44. The leads 68, 70 pass through sheath 58 and are of length to pass outside the body to conventional monitoring apparatus (not shown).

The installation of the stent 40 is identical with that described in connection with stent 10. That is, the entire assembly is inserted into the body and advanced until its end is adjacent an area of a body passage in which the stent/sensor is to be implanted, e.g., a blood vessel 74. The advance of the surrounding sheath 58 is then stopped, and the spool 44 is moved forwardly while the sheath 58 remains stationary. As the spool 44 is thus pushed out through the open end of the sheath 58, the spool 44 carries the stent 40 with it, because the flange 48 pushes the stent along the length of the spool 44. Once the flange 48 and the entirety of the stent 40 have cleared the open end of the sheath 58 as shown in FIG. 7, nothing restrains the stent 40 against expansion.

Inasmuch as the stent 40 is no longer maintained in its contracted condition, it expands under the influence of its inherent spring force to the full diameter of the vessel 74, illustrated in FIGS. 10-11. In the fully expanded condition of the stent 40, its outside surface contacts the inside surface of vessel 74, thereby securing the entire stent assembly 40 in place. At this point, the core 44, wire 52 and sheath 58 may be completely withdrawn from the body. This does not disturb the leads 68, 70, inasmuch as the groove 54 accommodates such withdrawal and insures that the leads are not subjected to undue stresses.

From the foregoing, it will be seen that this invention is one well adapted to attain all the ends and objects hereinabove set forth together with other advantages which are obvious and which are inherent to the structure.

It will be understood that certain features and subcombinations are of utility and may be employed without reference to other features and subcombinations. This is contemplated by and is within the scope of the claims.

Since many possible embodiments may be made of the invention without departing from the scope thereof, it is to be understood that all matter herein set forth or shown in the accompanying drawings is to be interpreted as illustrative and not in a limited sense.

We claim:

1. A stent and sensing device for placement in a body passage, comprising:

a tubular stent member presenting an inner surface and an outer surface adapted to contact the walls of a body passage, said stent having a relatively contracted condition permitting placement of the stent member within said passage, and an expanded condition whereby said stent is adapted to contact said body passage walls, said stent member being a flexible sheet wound into a multiple layer roll having said contracted and expanded conditions, said sheet having a spring force so that said sheet is urged toward the expanded condition thereof, said roll in the expanded condition thereof having at least two layers which overlap and bear against one another over a substantial portion of a circumference of the inner layer, said expanded roll adapted for securely contacting said body passage walls by virtue of said radial expansion tendency; and a sensing device secured to the inner surface of said tubular stent member and oriented for monitoring of a desired condition within the body.

2. The stent and sensing device of claim 1, including an elongated core supporting said multiple layer roll, said roll being tightly wound on the core in said contracted condition, with the expanded condition of said stent member presenting a diameter at least equal to the diameter of said body passage walls.

3. The stent and sensing device of claim 2, including releasable means for retaining said roll in the contracted condition thereof on said core while the core is being inserted into said body passage, and means for effecting release of said releasable means to permit the roll to expand and contact said body passage walls.

4. The stent and sensing device of claim 3, including a flange on said core and abutting one end of said roll when the latter is in said contracted condition thereof.

5. The stent and sensing device of claim 3, wherein said core is in the form of a tubular spool having an axial passage therethrough for receiving a guide wire along which the spool may be guided.

6. The stent and sensing device of claim 2, said core further having an elongated, axially extending groove in the outer surface thereof for accommodating electrical leads secured to said sensing device.

7. The stent and sensing device of claim 1, said sheet being constructed of metal foil.

8. The stent and sensing device of claim 1, said sensing device comprising a blood glucose sensor.

* * * * *